US00PP09054P

United States Patent [19]

Hesse

[11] Patent Number: Plant 9,054

[45] Date of Patent: Feb. 7, 1995

[54] CHRYSANTHEMUM PLANT NAMED DESERT ISLE

[75] Inventor: Peter S. Hesse, Nipomo, Calif.

[73] Assignee: Clearwater Nursery, Inc., Nipoma, Calif.

[21] Appl. No.: 178,875

[22] Filed: Jan. 7, 1994

[51] Int. Cl.[6] ..... A01H 5/00

[52] U.S. Cl. ..... Plt./82.3

[58] Field of Search ..... Plt. 82.2, 82.3

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Desert Isle. The new cultivar is distinguished by its yellow-orange ray floret color and yellow with green center disc floret.

1 Drawing Sheet

BACKGROUND OF THE NEW PLANT

Desert Isle was among the progeny of a cross made by Peter S. Hesse between the female parent Splendor (U.S. Plant Pat. No. 5,225) and the male parent was Hopscotch (U.S. Plant Pat. No. 5,816). The cross which produced Desert Isle was part of a breeding program conducted in Nipomo, Calif.

Desert Isle was discovered in a cultivated area and selected as one flowering plant within the progeny of the stated cross by Peter S. Hesse in November 1989, in a controlled environment in Nipomo, Calif.

The first act of asexual reproduction of Desert Isle was accomplished when vegetative cuttings were taken in January 1990, in a controlled environment in Nipomo, Calif. by Peter S. Hesse.

Horticultural examination of controlled flowerings of successive plantings has shown that the unique combination of characteristics as herein disclosed for Desert Isle are firmly fixed and are retained through successive generations of asexual reproduction.

Desert Isle has not been observed under all possible environmental conditions. The phenotype may vary significantly with variations in the environment such as temperature, light intensity and daylength.

The following observations, measurements and comparisons describe plants grown in a controlled environment in Nipomo, Calif. Unrooted cuttings were directly stuck into 6.5" pots and grown under the natural temperature and daylength prevailing in January through March of 1990.

Color designations are compared to the 1986 edition of R.H.S. Color Chart, first published in 1986 by The Royal Horticultural Society, London England. The NINE TM growth regulator referred to in the culturing procedures is 2,2-dimethyl hydrazide sold under the name of Daminozide or Alar and manufactured by Uniroyal.

The following traits have been repeatedly observed and are determined to be basic characteristics of Desert Isle, which in combination distinguish this Chrysanthemum as a new and distinct cultivar.

1. Flat capitulum form.
2. Daisy capitulum type.
3. Dark yellow orange to light yellow orange fully expanded outer ray florets.
4. Yellow daisy disc with green center.
5. Diameter across the face of capitulum of 12.5 cm.

6. Exceptional upright to spreading habit with an average of 4.0 breaks after a single pinch.
7. Flowering response of approximately 58 days from the start of short days.
8. Relative ease in controlling plant height from the bench such that the finished height will range from 9.5 inches to 11.5 inches above ground height.

DESCRIPTION OF THE PHOTOGRAPH

The accompanying photograph shows typical inflorescence and leaf characteristics of Desert Isle, with the colors being as nearly true as possible with illustrations of this type. The photograph shows Desert Isle grown as a pinched spray pot mum with 5 cuttings in a 6.5" pot.

DESCRIPTION OF THE PLANT

Of the commercial cultivars known to the inventor, the most similar in form, color, and habit to Desert Isle are the cultivars Splendor and Hopscotch. Reference is made to Table I which compares certain characteristics of Desert Isle to the same characteristics of the above mentioned cultivars.

The three cultivars were grown side by side in a controlled greenhouse environment. The growth regulator B-Nine TM was applied at a rate of 2500 ppm in three applications. Comparisons were made during the month of November 1993 in Encinitas, Calif.

TABLE I

| CHARACTERISTIC | HOPSCOTCH | DESERT ISLE | SPLENDOR |
|---|---|---|---|
| CAPITULUM FORM | flat | flat | flat |
| CAPITULUM TYPE | daisy | daisy | daisy |
| DIAMETER ACROSS FACE OF CAPITULUM | 7.5 cm | 12.5 cm | 12.2 cm |
| BRANCHING PATTERN | upright and spreading | upright and spreading | upright and spreading |
| BREAKS/PINCH | 4.4 | 4.0 | 4.0 |
| HEIGHT | 9.5 to 11.5 inches | 9.5 to 11.5 inches | 9.5 to 11.5 inches |
| DISC FLORET | yellow | yellow | yellow |
| NO. DISC FLORETS | 183.2 | 197.4 | 133.8 |
| LENGTH OF DISC FLORETS | 0.64 cm | 0.7 cm | 0.6 cm |
| RAY FLORET COLOR | front: yellow 9A | front: yellow | front: purple 75A |

TABLE I-continued

| CHARACTERISTIC | HOPSCOTCH | DESERT ISLE | SPLENDOR |
|---|---|---|---|
| | back: yellow 6A | orange 21A back: yellow 12B | back: purple 75D |
| NO. RAY FLORETS | 32.6 | 34.0 | 52.3 |
| SHAPE OF RAY FLORETS | elliptic | elliptic | elliptic |
| LENGTH OF RAY FLORETS | 3.85 cm | 5.3 cm | 5.2 cm |
| WIDTH OF RAY FLORETS | 1.43 cm | 1.3 cm | 1.5 cm |
| NUMBER OF FLOWERS/BREAK | 6.7 | 9.5 | 10.4 |
| LEAF COLOR | front: 147A back: 147B | front: 139A back: 138A | front: 139A back: 138A |
| MATURE LEAF LENGTH | up to 10.2 cm | up to 7.8 cm | up to 8.4 cm |
| MATURE LEAF WIDTH | 5.95 cm | 5.1 cm | 4.5 cm |
| RESPONSE: TREATMENT | 8.5 weeks: medium vigorous grower | 8.5 weeks: medium vigorous grower | 9.0 weeks: medium vigorous grower |

The three cultivars are similar in having a large flat, daisy capitulum. The diameter of the capitulum of Desert Isle tends to be as large as the capitulum of Splendor. Both Splendor and Desert Isle tend to have larger diameter capitulums than Hopscotch. All three cultivars have similar upright, spreading branching patterns and a similar number of breaks per pinch per plant. The finished plant height and the color of the disc florets are also similar for the three cultivars. Desert Isle tends to have more disc florets than either Hopscotch or Splendor. The length of the disc florets is similar for all three cultivars.

The front ray floret color for Desert Isle is yellow-orange 21A, for Hopscotch is yellow 9A, and for Splendor is purple 75A. The back ray floret color of Desert Isle is yellow 12B; for Hopscotch is yellow 6A; and for Splendor is purple 75D. Splendor has significantly more ray florets than either Hopscotch or Desert Isle. The ray florets of all three cultivars are elliptic. Desert Isle has ray florets that are similar in length to Splendor. Hopscotch has shorter ray florets. The width of the ray florets is similar for all three cultivars. The color of the leaves of Desert Isle is similar to Splendor. Hopscotch has darker leaves than either of the other cultivars. Hopscotch has the longest mature leaf length followed by Splendor, with Desert Isle having the shortest leaf. The three cultivars have similar leaf width. The response time from the start of short days is the same for Hopscotch and Desert Isle at 8.5 weeks while the response time of 9.0 weeks for Splendor is slightly higher.

THE PLANT

Classification:

*Botanical.*—*Dendranthema grandiflora.*

*Cultivar name.*—Desert Isle.

*Commercial.*—Flat daisy to be grown primarily as a Spray/CBR (center bud removed) or disbud pot mum.

Inflorescence:

*Capitulum.*—Form: Flat. Type: Daisy. Diameter across face: average of 12.5 cm measured as a disbud.

*Corolla of Ray Florets.*—General tonality from a distance of three meters: yellow–orange.

*Color.*—Front fully expanded outer ray floret: 21A. Back fully expanded outer ray floret: 12B. Disc floret color: Edge begins with 14A to Center Green of 141C.

General appearance:

*Height.*—When grown in a 6.5" pot with 1–4 applications of B-nine TM the total plant height may be maintained between 9.5 to 11.5 inches.

*Branching pattern.*—Upright and spreading with an average of 4.0 breaks when grown with one pinch.

*Foliage.*—Color (upper surface): 139A. Color (lower surface): 138A. Shape: See photograph.

Reproductive organs:

*Androecium.*—Present in disc floret only: Pollen, scent.

*Gynoecium.*—Present in both ray and disc florets.

What is claimed is:

1. A new and distinct Chrysanthemum plant named Desert Isle substantially as herein described and shown, characterized by its yellow-orange ray floret coloration and exceptional upright to spreading habit.

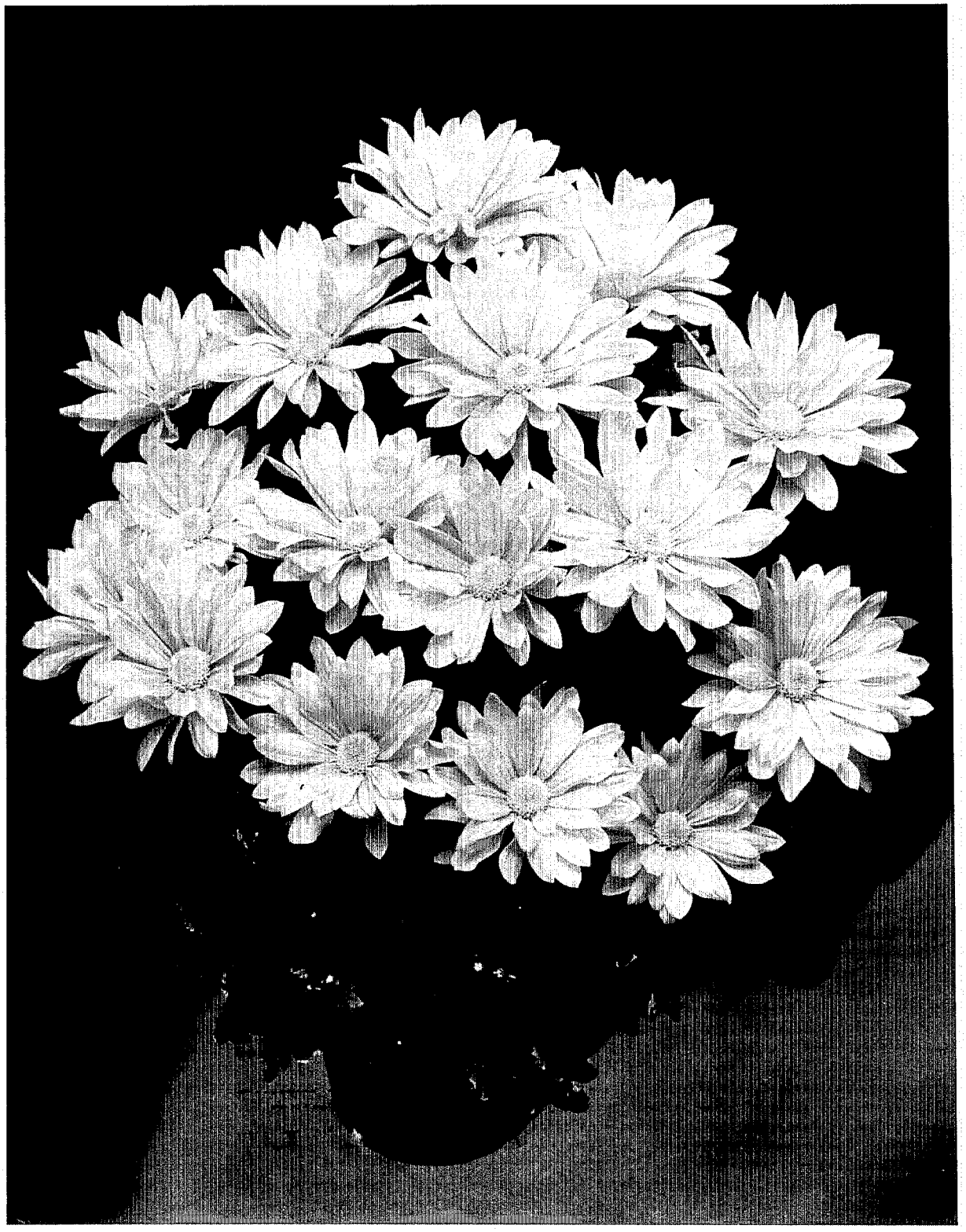

* * * * *